United States Patent
Brannan et al.

(10) Patent No.: US 9,192,308 B2
(45) Date of Patent: Nov. 24, 2015

(54) MICROWAVE-SHIELDED TISSUE SENSOR PROBE

(75) Inventors: Joseph D. Brannan, Erie, CO (US); Kenlyn S. Bonn, Lakewood, CO (US)

(73) Assignee: Covidien LP, Mansfield, MA (US)

( * ) Notice: Subject to any disclaimer, the term of this patent is extended or adjusted under 35 U.S.C. 154(b) by 771 days.

(21) Appl. No.: 13/430,810

(22) Filed: Mar. 27, 2012

(65) Prior Publication Data
US 2013/0261620 A1 Oct. 3, 2013

(51) Int. Cl.
*A61B 18/14* (2006.01)
*A61B 5/01* (2006.01)
(Continued)

(52) U.S. Cl.
CPC ............... *A61B 5/01* (2013.01); *A61B 18/1815* (2013.01); *A61B 2018/00642* (2013.01); *A61B 2018/00702* (2013.01); *A61B 2018/00797* (2013.01); *A61B 2018/00809* (2013.01); *A61B 2018/00815* (2013.01); *A61B 2018/00821* (2013.01); *A61B 2018/1861* (2013.01); *A61B 2018/1869* (2013.01)

(58) Field of Classification Search
CPC ................. A61B 2018/00791; A61B 18/1206; A61B 18/1492; A61B 2018/00083; A61B 2018/00107; A61B 2017/00084; A61B 2017/00088; A61B 2017/00092; A61B 2018/00577; A61B 18/1402; A61B 2017/00292; A61B 2018/00636; A61B 2018/00821; A61B 2018/00101; A61B 2018/00095; A61B 2018/00809; A61B 2018/00815; A61N 1/06; G01K 1/026
USPC ............................................... 606/32–34, 41
See application file for complete search history.

(56) References Cited

U.S. PATENT DOCUMENTS

| D223,367 S | 4/1972 | Kountz |
| D263,020 S | 2/1982 | Rau, III |

(Continued)

FOREIGN PATENT DOCUMENTS

| CN | 1103807 A | 6/1995 |
| DE | 390937 C | 3/1924 |

(Continued)

OTHER PUBLICATIONS

U.S. Appl. No. 13/400,223, filed Feb. 20, 2012, Anthony B. Ross.
(Continued)

*Primary Examiner* — Deborah Malamud (57) ABSTRACT

A tissue sensor probe and corresponding electromagnetic surgical ablation system are disclosed. The system includes an ablation probe coupled to a generator, a controller coupled to the generator, and a tissue sensor probe coupled to the controller. The tissue sensor probe includes an electrically-conductive enclosure configured to shield a temperature sensor from electromagnetic radiation produced by the ablation probe. At least a portion of the electrically-conductive enclosure is made of a high thermal-conductivity material. A material of high thermal-conductivity is disposed in the electrically-conductive enclosure in thermal association with the thermally-conductive material of the electrically-conductive enclosure. The temperature sensor is disposed in the material of high thermal conductivity so as to electrically isolate the temperature sensor from the enclosure. The temperature sensor provides tissue temperature to the controller, which monitors tissue temperature to determine tissue status and activates and deactivates the generator based on the tissue status.

22 Claims, 4 Drawing Sheets

(51) Int. Cl.
*A61B 18/18* (2006.01)
*A61B 18/00* (2006.01)

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| D354,218 S | 1/1995 | Van de Peer | |
| 5,769,847 A * | 6/1998 | Panescu et al. | 606/42 |
| 6,053,912 A | 4/2000 | Panescu et al. | |
| D424,693 S | 5/2000 | Pruter | |
| D424,694 S | 5/2000 | Tetzlaff et al. | |
| D425,201 S | 5/2000 | Tetzlaff et al. | |
| D449,886 S | 10/2001 | Tetzlaff et al. | |
| D457,958 S | 5/2002 | Dycus et al. | |
| D457,959 S | 5/2002 | Tetzlaff et al. | |
| D487,039 S | 2/2004 | Webster et al. | |
| D496,997 S | 10/2004 | Dycus et al. | |
| D499,181 S | 11/2004 | Dycus et al. | |
| D525,361 S | 7/2006 | Hushka | |
| D531,311 S | 10/2006 | Guerra et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| D634,010 S | 3/2011 | DeCarlo | |
| 2003/0088244 A1 | 5/2003 | Swanson et al. | |
| 2007/0270971 A1 | 11/2007 | Trieu et al. | |
| 2011/0208180 A1 | 8/2011 | Brannan | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 04303882 C2 | 2/1995 |
| DE | 4339049 A1 | 5/1995 |
| DE | 29616210 U1 | 11/1996 |
| DE | 19608716 C1 | 4/1997 |
| DE | 19751106 A1 | 5/1998 |
| DE | 19717411 A1 | 11/1998 |
| DE | 19751108 A1 | 5/1999 |
| DE | 19801173 C1 | 7/1999 |
| DE | 19848540 A1 | 5/2000 |
| DE | 10224154 A1 | 12/2003 |
| DE | 10310765 A1 | 9/2004 |
| DE | 10328514 B3 | 3/2005 |
| DE | 102004022206 A1 | 12/2005 |
| DE | 202005015147 U1 | 2/2006 |
| DE | 102009015699 A1 | 5/2010 |
| EP | 0150253 A2 | 8/1985 |
| EP | 0246350 A1 | 11/1987 |
| EP | 0521264 A2 | 1/1993 |
| EP | 0556705 A1 | 8/1993 |
| EP | 0558429 A1 | 9/1993 |
| EP | 0 648 515 A1 | 4/1995 |
| EP | 0 836 868 A2 | 4/1998 |
| EP | 0 882 955 A1 | 12/1998 |
| EP | 1 159 926 A2 | 12/2001 |
| EP | 2345454 A1 | 7/2011 |
| EP | 2371318 A1 | 10/2011 |
| FR | 179 607 | 11/1906 |
| FR | 1 275 415 A | 11/1961 |
| FR | 1 347 865 A | 1/1964 |
| FR | 2 235 669 A1 | 1/1975 |
| FR | 2 276 027 A1 | 1/1976 |
| FR | 2 313 708 A1 | 12/1976 |
| FR | 2 502 935 A1 | 10/1982 |
| FR | 2 517 953 A1 | 6/1983 |
| FR | 2 573 301 A1 | 5/1986 |
| FR | 2 862 813 A1 | 5/2005 |
| FR | 2 864 439 A1 | 7/2005 |
| JP | 5-5106 | 1/1993 |
| JP | 05-40112 | 2/1993 |
| JP | 06343644 A | 12/1994 |
| JP | 07265328 A | 10/1995 |
| JP | 08056955 A | 3/1996 |
| JP | 08252263 A | 10/1996 |
| JP | 09000492 A | 1/1997 |
| JP | 09010223 A | 1/1997 |
| JP | 11244298 A | 9/1999 |
| JP | 2000350732 A | 12/2000 |
| JP | 2001003776 A | 1/2001 |
| JP | 2001008944 A | 1/2001 |
| JP | 2001029356 A | 2/2001 |
| JP | 2001037775 A | 2/2001 |
| JP | 2001128990 A | 5/2001 |
| JP | 2001231870 A | 8/2001 |
| JP | 2008142467 A | 6/2008 |
| SU | 166452 | 11/1964 |
| SU | 401367 A1 | 10/1973 |
| SU | 727201 A2 | 4/1980 |
| WO | 9509576 A1 | 4/1995 |
| WO | 00/36985 A2 | 6/2000 |
| WO | 01/95810 A2 | 12/2001 |
| WO | 2008/008545 A2 | 1/2008 |
| WO | 2010/035831 A1 | 4/2010 |
| WO | 2010/129348 A1 | 11/2010 |

OTHER PUBLICATIONS

U.S. Appl. No. 13/419,981, filed Mar. 14, 2012, Joseph D. Brannan.
U.S. Appl. No. 13/440,690, filed Apr. 5, 2012, Joseph D. Brannan.
U.S. Appl. No. 13/460,440, filed Apr. 30, 2013, Arnold V. DeCarlo.
U.S. Appl. No. 13/464,021, filed May 4, 2012, Joseph D. Brannan.
U.S. Appl. No. 13/477,260, filed May 22, 2012, William R. Reid, Jr.
U.S. Appl. No. 13/477,320, filed May 22, 2012, Joseph D. Brannan.
U.S. Appl. No. 13/711,086, filed Dec. 11, 2012, Joseph D. Brannan.
U.S. Appl. No. 13/791,212, filed Mar. 8, 2013, Brannan.
U.S. Appl. No. 13/835,183, filed Mar. 15, 2013, Arts.
U.S. Appl. No. 13/835,513, filed Mar. 15, 2013, Brannan.
U.S. Appl. No. 13/836,014, filed Mar. 15, 2013, Arts.
U.S. Appl. No. 13/836,353, filed Mar. 15, 2013, Arts.
U.S. Appl. No. 13/839,562, filed Mar. 15, 2013, Zheng.
U.S. Appl. No. 13/853,363, filed Mar. 29, 2013, Kim.
U.S. Appl. No. 13/856,363, filed Apr. 3, 2013, Peterson.
U.S. Appl. No. 13/867,834, filed Jul. 22, 2013, Brannan.
U.S. Appl. No. 13/871,142, filed Apr. 26, 2013, Ohri.
U.S. Appl. No. 13/886,080, filed May 2, 2013, Bahney.
U.S. Appl. No. 13/889,989, filed May 8, 2013, Lee.

(56) References Cited

OTHER PUBLICATIONS

U.S. Appl. No. 13/903,668, filed May 28, 2013, Podhajsky.
U.S. Appl. No. 13/904,478, filed May 29, 2013, Ohri.
U.S. Appl. No. 13/908,463, filed Jun. 3, 2013, Brannan.
U.S. Appl. No. 13/908,555, filed Jun. 3, 2013, Dunning.
U.S. Appl. No. 13/920,367, filed Jun. 18, 2013, Sharonov.
U.S. Appl. No. 13/920,411, filed Jun. 18, 2013, Sharonov.
U.S. Appl. No. 13/922,006, filed Jun. 19, 2013, Nau.
U.S. Appl. No. 13/942,833, filed Jul. 16, 2013, Sharonov.
U.S. Appl. No. 13/942,864, filed Jul. 16, 2013, Sharonov.
U.S. Appl. No. 13/943,452, filed Jul. 16, 2013, Behnke.
U.S. Appl. No. 13/945,519, filed Jul. 18, 2013, Prakash.
U.S. Appl. No. 13/945,718, filed Jul. 18, 2013, Rossetto.
LigaSureTM Vessel Sealing System, the Seal of Confidence in General, Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire: product description, 1 page.
Medtrex Brochure "The O.R. Pro 300" 1 page, Sep. 1998.
Michael Choti, "Abdominoperineal Resection with the LigaSureTM Vessel Sealing System and LigaSureTM Atlas 20 cm Open Instrument" Innovations That Work, Jun. 2003.
Muller et al., "Extended Left Hemicolectomy Using the LigaSureTM Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.
Ni Wei et al., "A Signal Processing Method for the Coriolis Mass Flowmeter Based on a Normalized . . . " Journal of Applied Sciences-Yingyong Kexue Xuebao, Shangha CN, vol. 23, No. 2: (Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thermoradiotheray and Thermochemotherapy (1995) vol. I, Biology, Physiology, Physics, pp. 279-320.
Palazzo et al., "Randomized clinical trial of LigaSureTM versus open haemorrhoidectomy" British Journal of Surgery 2002, 89, 154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).

R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSureTM Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817•825.
Urologix, Inc.-Medical Professionals: TargisTM Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation-'COA-COMP'" Neurosurgical Review 7:2-3 (1984) pp. 187-190.
W. Scott Helton, "LigaSureTM Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
U.S. Appl. No. 08/136,098; Oct. 14, 1993; Roger A. Stern.
U.S. Appl. No. 08/483,742; Jun. 7, 1995; Roger A. Stern.
European Search Report from corresponding EP 13 15 9715 mailed Jun. 18, 2013.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.

(56) References Cited

OTHER PUBLICATIONS

Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok™ Breast Lesion Needle/ Wire Localizer, Namic ® Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003. cited by applicant.
B. Levy M.D. et al., "Update on Hysterectomy New Technologies and Techniques" OBG Management, Feb. 2003. cited by applicant.
B. Levy M.D., "Use of a New Vessel Ligation Device During Vaginal Hysterectomy" FIGO 2000, Washington, D.C. cited by applicant.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999. cited by applicant.
Bergdahl et al., "Studies on Coagulation and the Development of an Automatic Computerized Bipolar Coagulator" Journal of Neurosurgery 75:1 (Jul. 1991), pp. 148-151. cited by applicant.
Bulletin of the American Physical Society, vol. 47, No. 5, Aug. 2002, p. 41. cited by applicant.
C. F. Gottlieb et al., "Interstitial Microwave Hyperthermia Applicators having Submillimetre Diameters", Int. J. Hyperthermia, vol. 6, No. 3, pp. 707-714, 1990. cited by applicant.
C. H. Durney et al., "Antennas for Medical Applications", Antenna Handbook: Theory Application and Design, p. 24-40, Van Nostrand Reinhold, 1988 New York, V.T. Lo, S.W. Lee. cited by applicant.
Carbonell et al., "Comparison of the Gyrus PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center, Charlotte, NC 2003. cited by applicant.
Carus et al., "Initial Experience With the LigaSure.TM. Vessel Sealing System in Abdominal Surgery" Innovations That Work, Jun. 2002. cited by applicant.
Chicharo et al., "A Sliding Goertzel Algorithm" Aug. 1996 DOS pp. 283-297 Signal Processing, Elsevier Science Publishers B.V. Amsterdam, NL, vol. 52, No. 3. cited by applicant.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428. cited by applicant.
Chung et al., "Clinical Experience of Sutureless Closed Hemorrhoidectomy with LigaSureTM" Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw-Hill, vol. 111, (1984), pp. 2490-2499. cited by applicant.
Cosman et al., "Radiofrequency Lesion Generation and its Effect on Tissue Impedance", Applied Neurophysiology, 51:230-242, 1988. cited by applicant.
Cosman et al., "Theoretical Aspects of Radiofrequency Lesions in the Dorsal Root Entry Zone" Neurosurgery 15: (1984), pp. 945-950. cited by applicant.
Crawford et al., "Use of the LigaSure.TM. Vessel Sealing System in Urologic Cancer Surger" Grand Rounds in Urology 1999, vol. 1, Issue 4, pp. 10-17. cited by applicant.
Dulemba et al., "Use of a Bipolar Electrothermal Vessel Sealer in Laparoscopically Assisted Vaginal Hysterectomy" Sales/Product Literature; Jan. 2004. cited by applicant.
E. David Crawford, "Evaluation of a New Vessel Sealing Device in Urologic Cancer Surgery" Sales/Product Literature 2000. cited by applicant.
E. David Crawford, "Use of a Novel Vessel Sealing Technology in Management of the Dorsal Veinous Complex" Sales/Product Literature 2000. cited by applicant.
Esterline, "Light Key Projection Keyboard" Advanced Input Systems, located at: <http://www.advanced-inputcom/lightkey> 2002.
Esterline Product Literature, "Light Key: Visualize a Virtual Keyboard. One With No Moving Parts", Nov. 1, 2003; 4 pages. cited by applicant.
Geddes et al., "The Measurement of Physiologic Events by Electrical Impedence" Am. J. MI, Jan. Mar. 1964, pp. 16-27. cited by applicant.
Goldberg et al., "Image-guided Radiofrequency Tumor Ablation: Challenges and Opportunities—Part I", (2001) J Vasc. Interv. Radiol, vol. 12, pp. 1021-1032. cited by applicant.
Goldberg et al. (1995) "Saline-enhanced RF Ablation: Demonstration of Efficacy and Optimization of Parameters", Radiology, 197(P): 140 (Abstr). cited by applicant.
Goldberg et al., "Tissue Ablation with Radiofrequency: Effect of Probe Size, Gauge, Duration, and Temperature on Lesion Volume" Acad Radio (1995) vol. 2, No. 5, pp. 399-404. cited by applicant.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSureTM Vessel Sealing System: A Case Report" Innovations That Work, Feb. 2002.
Humphries Jr. et al., "Finite-Element Codes to Model Electrical Heating and Non-Llnear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSureTM Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSureTM Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSureTM Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSureTM System Used in Laparoscopic 1st and 2nd Stage Orchiopexy" Innovations That Work, Nov. 2002.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.
Koyle et al., "Laparoscopic Palomo Varicocele Ligation in Children and Adolescents" Pediatric Endosurgery & Innovative Techniques, vol. 6, No. 1, 2002.

* cited by examiner

MICROWAVE-SHIELDED TISSUE SENSOR PROBE

BACKGROUND

1. Technical Field

The present disclosure relates to systems and methods for providing energy to biological tissue and, more particularly, to systems and methods for precisely sensing thermal parameters of tissue during a microwave ablation procedure.

2. Background of Related Art

Energy-based tissue treatment is well known in the art. Various types of energy (e.g., electrical, ultrasonic, microwave, cryogenic, thermal, laser, etc.) are applied to tissue to achieve a desired result. Electrosurgery involves application of high radio frequency electrical current to a surgical site to cut, ablate, coagulate or seal tissue. In monopolar electrosurgery, a source or active electrode delivers radio frequency energy from the electrosurgical generator to the tissue and a return electrode carries the current back to the generator. In monopolar electrosurgery, the source electrode is typically part of the surgical instrument held by the surgeon and applied to the tissue to be treated. A return electrode is placed remotely from the active electrode to carry the current back to the generator. In tissue ablation electrosurgery, the radio frequency energy may be delivered to targeted tissue by an antenna or probe.

There are several types of microwave antenna assemblies in use, e.g., monopole, dipole and helical, which may be used in tissue ablation applications. In monopole and dipole antenna assemblies, microwave energy generally radiates perpendicularly away from the axis of the conductor. Monopole antenna assemblies typically include a single, elongated conductor. A typical dipole antenna assembly includes two elongated conductors, which are linearly aligned and positioned end-to-end relative to one another with an electrical insulator placed between them. Helical antenna assemblies include a helically-shaped conductor connected to a ground plane. Helical antenna assemblies can operate in a number of modes including normal mode (broadside mode), in which the field radiated by the helix is maximum in a perpendicular plane to the helix axis, and axial mode (end fire mode), in which maximum radiation is along the helix axis. The tuning of a helical antenna assembly may be determined, at least in part, by the physical characteristics of the helical antenna element, e.g., the helix diameter, the pitch or distance between coils of the helix, and the position of the helix in relation to the probe assembly to which the helix is mounted.

The typical microwave antenna has a long, thin inner conductor that extends along the longitudinal axis of the probe and is surrounded by a dielectric material. An outer conductor surrounds the dielectric material and extends along the axis of the probe. In another variation of the probe that provides effective outward radiation of energy or heating, a portion or portions of the outer conductor are selectively removed. This type of construction is typically referred to as a "leaky waveguide" or "leaky coaxial" antenna. Another variation on the microwave antenna probe involves having the tip formed in a uniform spiral pattern, such as a helix, to provide the necessary configuration for effective radiation. This variation can be used to direct energy in a particular direction, e.g., perpendicular to the axis, in a forward direction (i.e., towards the distal end of the antenna), or any combination of these directions.

Invasive procedures and devices have been developed in which a microwave antenna probe is either inserted directly into a point of treatment via a normal body orifice or percutaneously inserted. Such invasive procedures and devices potentially provide better temperature control of the tissue being treated. Because of the small difference between the temperature required for denaturing malignant cells and the temperature injurious to healthy cells, a known heating pattern and predictable temperature control is important so that heating is confined to the tissue to be treated. For instance, hyperthermia treatment at the threshold temperature of about 41.5° C. generally has little effect on most malignant growth of cells. However, at slightly elevated temperatures above the approximate range of 43° C. to 45° C. or with rapid bursts of elevated temperatures, thermal damage to most types of normal cells is routinely observed. Accordingly, great care must be taken not to exceed these temperatures along the length of the ablation probe when it is placed adjacent to healthy tissue.

In the case of tissue ablation, a high radio frequency electrical current in the range of about 500 MHz to about 10 GHz is applied to a targeted tissue site to create an ablation volume, which may have a particular size and shape. The ablation volume is correlated to antenna design, antenna tuning, antenna impedance and tissue impedance. Tissue impedance may change during an ablation procedure due to a number of factors, e.g., tissue denaturization or desiccation occurring from the absorption of microwave energy by tissue. Changes in tissue impedance may cause an impedance mismatch between the probe and tissue, which may affect delivery of microwave ablation energy to targeted tissue. The temperature and/or impedance of targeted tissue, and of non-targeted tissue and adjacent anatomical structures, may change at varying rates, which may be greater, or less than, expected rates. A surgeon may need to perform an ablation procedure in an incremental fashion in order to avoid exposing targeted tissue and/or adjacent tissue to excessive temperatures and/or denaturation. In certain circumstances, a surgeon may need to rely on experience and/or published ablation probe parameters to determine an appropriate ablation protocol (e.g., ablation time, ablation power level, and the like) for a particular patient.

One way to monitor and control the temperature of tissue during a tissue ablation procedure is to provide feedback from a tissue sensor probe. If, however, the tissue sensor probe is positioned near a microwave ablation probe, the electromagnetic fields produced by the microwave ablation probe may reduce the accuracy and precision of the measurements of the tissue sensor probe either through direct thermal agitation of the thermal physics of the tissue sensor probe or through induced electrical current in the tissue sensor probe. One solution to this problem is to maintain an appropriate distance between the tissue sensor probe and the electromagnetic fields produced by the microwave field during a surgical procedure. It is difficult, however, to predict the location and boundary of this electromagnetic field. In addition, electromagnetic energy from other sources may interfere with the operation of the tissue sensor probe.

SUMMARY

The disclosed tissue sensor probe and corresponding surgical ablation system increases the speed and accuracy of temperature measurements taken near an ablation probe during a microwave ablation procedure. This is achieved by shielding a temperature sensor within the probe from electromagnetic radiation produced by the microwave ablation probe and maximizing the response time of thermal energy transfer to the temperature sensor.

In one aspect, the present disclosure is directed to an electromagnetic surgical ablation system that includes a tissue sensor probe that is configured to accurately sense tissue temperature at or near an ablation surgical site. The electromagnetic surgical ablation system also includes a generator that selectively provides surgical ablation energy to an ablation probe. The surgical ablation system further includes an ablation probe operatively coupled to the generator and configured to receive ablation energy from the generator and to deliver the ablation energy to tissue. The surgical ablation system further includes a controller operatively coupled to the generator. The controller includes a processor and a memory operatively coupled to the processor.

The tissue sensor probe is operatively coupled to the controller. The tissue sensor probe includes an electrically-conductive enclosure. At least a portion of the electrically-conductive enclosure is formed of a thermally-conductive material. The electrically-conductive enclosure may include an elongated cylindrical shaft having a distal end and a proximal end, a thermally-conductive tip electrically coupled to the distal end of the elongated cylindrical shaft, and a cap electrically coupled to the proximal end of the elongated cylindrical shaft. At least one of the electrically-conductive elongated cylindrical shaft, the electrically-conductive tip, and the electrically-conductive cap may include at least one of stainless steel, copper, and aluminum.

The tissue sensor probe also includes a material of high thermal conductivity disposed in the electrically-conductive enclosure and in thermal association with the thermally-conductive material. At least a portion of the material of high thermal conductivity may be disposed within the electrically-conductive tip. The material of high thermal conductivity may have low electrical conductivity. The material of high thermal conductivity may include at least one of silver, gold, carbon nanotube, diamond, copper, aluminum, a thermally-conductive gel, and a thermally-conductive polymer.

The tissue sensor probe further includes a temperature sensor disposed in the material of high thermal conductivity and electrically isolated from the electrically-conductive enclosure. The temperature sensor may include a plurality of temperature sensors disposed along the length of the electrically-conductive elongated cylindrical shaft.

The temperature sensor may be configured to provide a temperature sensor signal corresponding to a temperature of body tissue. The temperature sensor may include at least one of a fluoroptic temperature sensor, a thermocouple, a thermistor, a resistance temperature detector, or an infrared thermometer.

The surgical ablation system may further include an actuator operatively coupled to the controller and configured to selectively activate the generator. The actuator may be selected from a group consisting of a handswitch, a footswitch, and an orally-activated switch. The tissue sensor probe may also include a handle disposed at a proximal end of the tissue sensor probe. The handle may include a grip-enhancing feature.

In another aspect, the present disclosure is directed to a tissue sensor probe. The tissue sensor probe includes an electrically-conductive elongated cylindrical shaft having a distal end and a proximal end. The tissue sensor probe also includes an electrically-conductive tip coupled to the distal end of the electrically-conductive cylindrical shaft. The electrically-conductive tip closes the distal end of the electrically-conductive cylindrical shaft and has a high thermal conductivity. The temperature sensor further includes an electrically-conductive cap coupled to the proximal end of the elongated cylindrical shaft to close the proximal end of the electrically-conductive cylindrical shaft. At least one of the electrically-conductive elongated cylindrical shaft, the electrically-conductive tip, and the electrically-conductive cap may be composed of at least one of stainless steel, copper, and aluminum.

The tissue sensor probe also includes a material of high thermal conductivity disposed in the distal end of the elongated cylindrical shaft. The material of high thermal conductivity is disposed in the distal end of the elongated cylindrical shaft so that it is in thermal association with the electrically-conductive tip.

The tissue sensor probe further includes a temperature sensor disposed in the material of high thermal conductivity and electrically isolated from the electrically-conductive cylindrical shaft and the electrically-conductive tip. In some embodiments, the temperature sensor may be configured to provide a temperature sensor signal corresponding to a temperature of body tissue. The temperature sensor may include at least one of a fluoroptic temperature sensor, a thermocouple, a thermistor, a resistive temperature detector, and an infrared thermometer. In some embodiments, the temperature sensor may include a plurality of temperature sensors disposed along the length of the electrically-conductive elongated cylindrical shaft configured to measure a temperature profile or gradient.

The tissue sensor probe may include a handle disposed at a proximal end of the elongated cylindrical shaft. In some embodiments, the material of high thermal conductivity may have low electrical conductivity. The material of high thermal conductivity may include at least one of silver, gold, carbon nanotube, diamond, copper, and aluminum. At least a portion of the material of high thermal conductivity may be disposed within the electrically-conductive tip.

BRIEF DESCRIPTION OF THE DRAWINGS

The above and other aspects, features, and advantages of the present disclosure will become more apparent in light of the following detailed description when taken in conjunction with the accompanying drawings in which.

DETAILED DESCRIPTION

Particular embodiments of the present disclosure will be described hereinbelow with reference to the accompanying drawings; however, it is to be understood that the disclosed embodiments are merely exemplary of the disclosure, which may be embodied in various forms. Well-known functions or constructions are not described in detail to avoid obscuring the present disclosure in unnecessary detail. Therefore, specific structural and functional details disclosed herein are not to be interpreted as limiting, but merely as a basis for the claims and as a representative basis for teaching one skilled in the art to variously employ the present disclosure in virtually any appropriately detailed structure.

In the drawings and in the descriptions that follow, the term "proximal," as is traditional, shall refer to the end of the instrument that is closer to the user, while the term "distal" shall refer to the end that is farther from the user.

Figure 1:
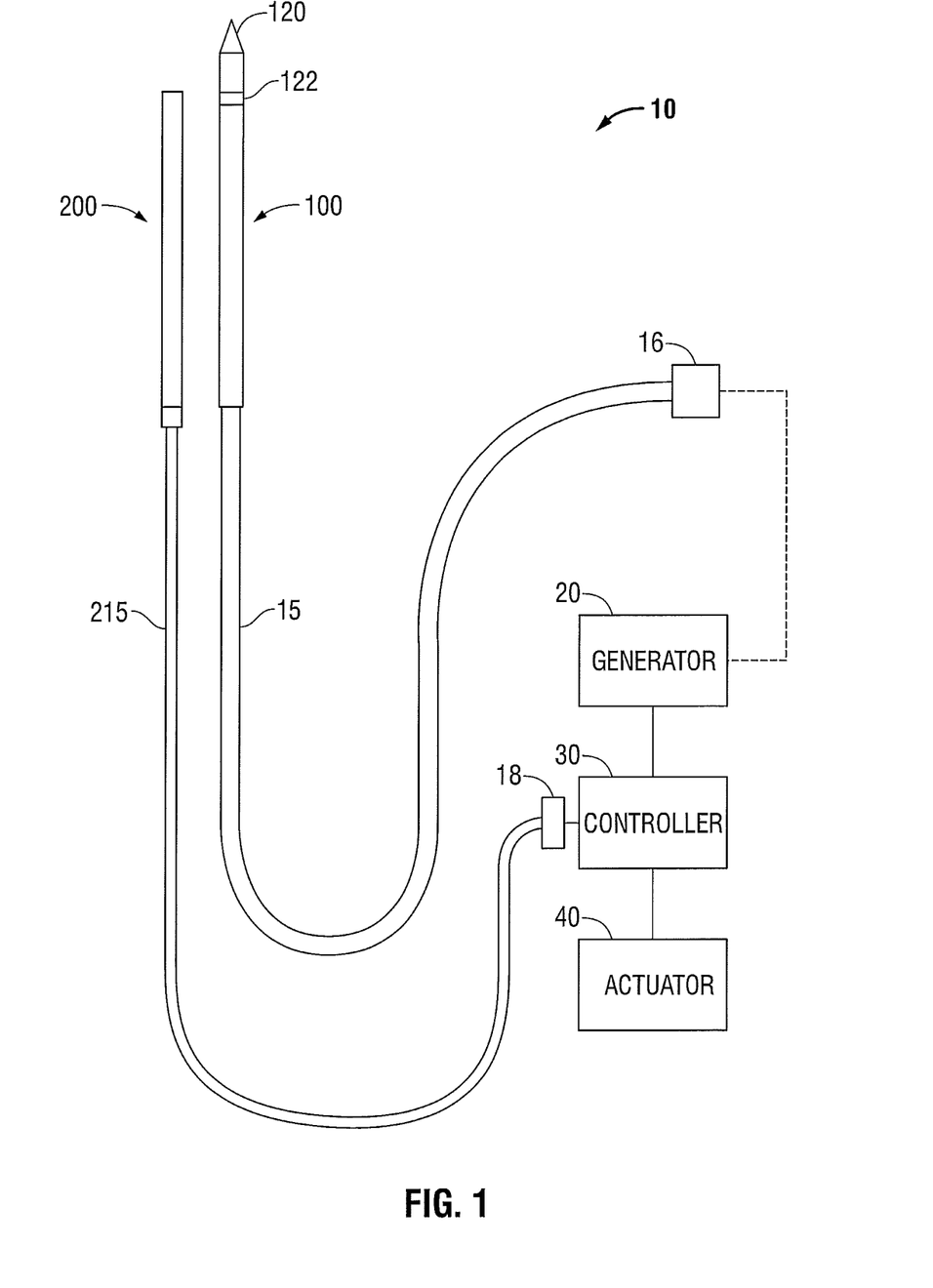
FIG. 1 is a diagram of a microwave ablation system having an electromagnetic surgical ablation probe and a tissue sensor probe in accordance with embodiments of the present disclosure.

FIG. 1 shows an embodiment of a microwave ablation system 10 in accordance with the present disclosure. The microwave ablation system 10 includes an electromagnetic surgical ablation probe 100 having a tapered distal tip 120 and a feed point 122. The ablation probe 100 is operatively connected by a cable 15 to connector 16, which may further operatively connect ablation probe 100 to a generator assembly 20. Generator assembly 20 may be a source of ablation energy, e.g., microwave or RF energy in the range of about 915 MHz to about 2.45 GHz. The disclosed system 10 includes a tissue sensor probe 200 that is configured to sense at least one operative parameter, e.g., a tissue temperature. In other embodiments, the tissue sensor probe 200 may be configured to sense a tissue dielectric parameter, e.g., a relative permittivity, a dielectric constant, a dielectric loss factor and/or conductivity. The tissue sensor probe 200 is operatively connected by a cable 215 to connector 18, which may further operatively connect tissue sensor probe 200 to a controller assembly 30. An actuator 40 is operatively coupled to the controller to enable a user, e.g., a surgeon, to selectively activate and de-activate the delivery of ablation energy to patient tissue. Controller 30 is operatively coupled to generator 20 to enable communication therebetween, such as without limitation, a control signal and/or a status signal.

Figure 2:
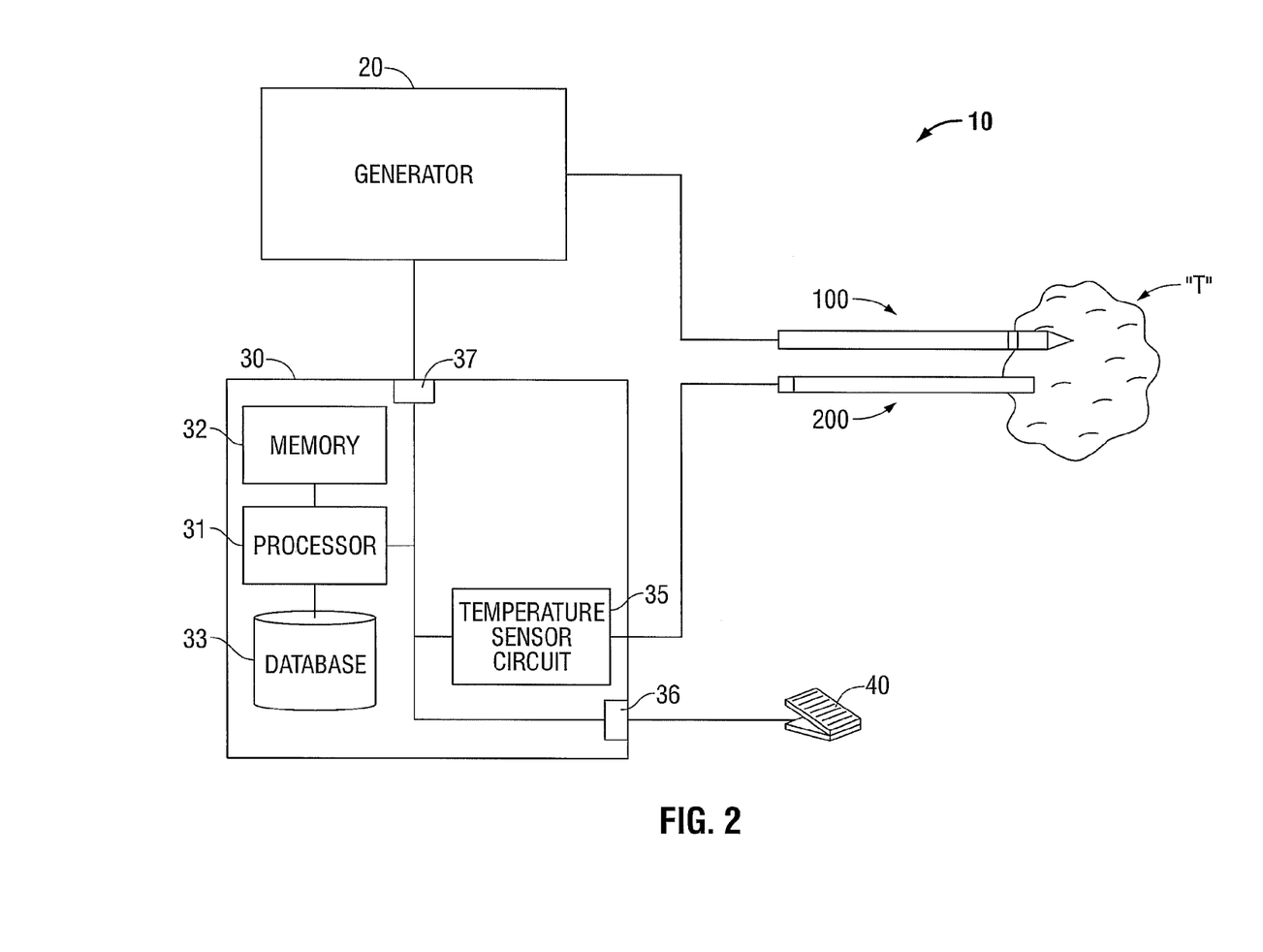
FIG. 2 is a block diagram of a microwave ablation system having an electromagnetic surgical ablation probe and a tissue sensor probe in accordance with embodiments of the present disclosure.

FIG. 2 illustrates a functional block diagram of an ablation system 10 in accordance with the present disclosure. The system 10 includes a controller 30 that includes one or more processors 31 operatively coupled to memory 32, a database 33, and a temperature sensor circuit 35. In other embodiments, the controller 30 may include one or more processors 31 operatively coupled to other sensor circuits (not explicitly shown), e.g., a dielectric sensor circuit, that are coupled to corresponding sensors in the tissue sensor probe 200. Processor(s) 31 may be configured to execute a set of programmed instructions for performing a method of microwave ablation as disclosed herein.

Controller 30 includes actuator interface 36 that is adapted to facilitate operative coupling with actuator 40 and/or a generator interface 37 that is adapted to facilitate operative coupling with generator 20. Actuator 40 may be any suitable actuator, such as without limitation, a footswitch, a handswitch (which may be mounted on an ablation probe 100 and/or a tissue sensor probe 200), an orally-activated switch (e.g., a bite-activated switch and/or a breath-actuated switch), and the like.

The processor(s) 31, memory 32, database 33, temperature sensor circuit 35, actuator interface 36 and/or generator interface 37 may be separate components or may be integrated, such as in one or more integrated circuits. The various components in the controller 30 may be coupled by one or more communication buses or signal lines 38. Memory 30 and/or database 33 may include a set of executable instructions for performing a method of microwave ablation as described herein. One or more elements of ablation system 10 may be coupled using hard-wired connections and/or a wireless link. During use, tissue sensor probe 200 may be positioned in tissue T in proximity to ablation probe 100 to obtain at least one tissue parameter.

Embodiments of tissue sensor probe 200 in accordance with the present disclosure are now described with reference to FIGS. 3 and 4. The tissue sensor probe 200 may be a needle-like device having a small gauge size (e.g., 17 gauge or smaller). The tissue sensor probe 200 includes a temperature sensor 231 and interfaces with a microwave generator and controller to enable feedback and control using tissue temperature measurements from the tissue sensor probe 200. For example, the user may use the controller to set limits on the temperature of target tissue and apply high frequency energy to the target tissue based on temperature limits and the measured tissue temperature.

Figure 3:
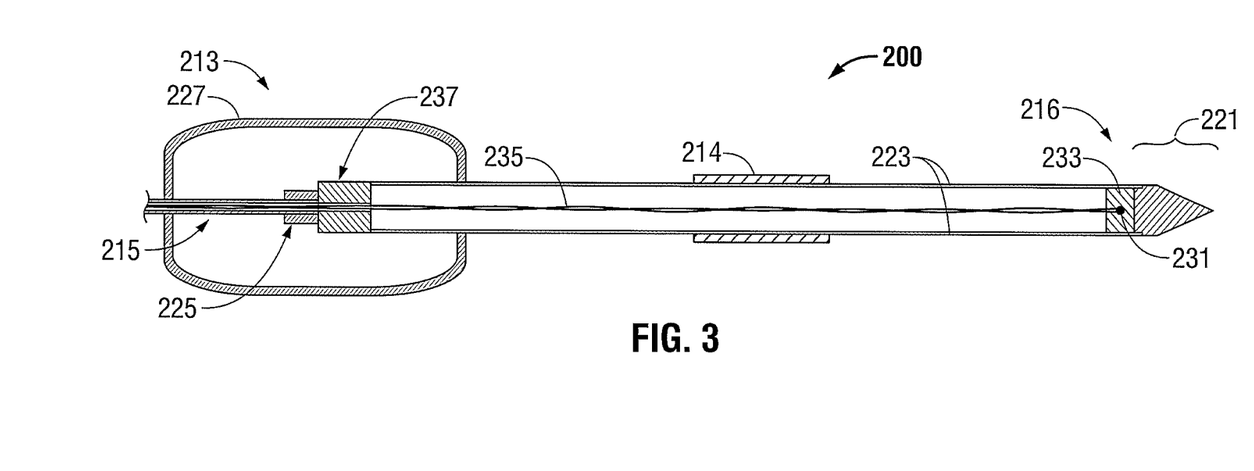
FIG. 3 is a side, cross-sectional view of a tissue sensor probe in accordance with embodiments of the present disclosure.

Referring to FIG. 3, the tissue sensor probe 200 is configured to form a "Faraday cage" or a "Faraday shield." A Faraday cage is an enclosure or a container made of electrically-conductive material that can shield its interior from external electromagnetic radiation if the electrically-conductive material has an appropriate thickness. In operation, an external electrical field causes the electrical charges within the Faraday cage's electrically-conductive material to redistribute so as to cancel the external electrical field's effects in the Faraday cage's interior.

The tissue sensor probe 200 includes an electrically-conductive enclosure configured as a Faraday cage, which contains a temperature sensor 231. In this way, the temperature sensor 231 is isolated from any electromagnetic radiation, including microwave radiation, originating external to the probe 200. The probe 200 includes an elongated, generally-cylindrical shaft 223 having a proximal end 213 and a distal end 216. In some embodiments, the elongated shaft 223 is a cylindrical hypo-tube made of stainless steel or other electrically-conductive metal such as aluminum or copper.

The distal end 216 of the shaft 223 includes an electrically-conductive tip 221, such as a metal trocar tip. The tip 221 is made of an electrically-conductive material that also has high thermal conductivity, such as copper, silver, gold, or any alloys of these materials. In some embodiments, the electrically-conductive material may also have physical properties that allow the tip 221 to keep its sharpness for long periods.

An electrical connection is made completely around the junction between the tip 221 and the elongated shaft 223, either by close physical contact or by soldering or laser welding, to form a tight, electrically-conductive enclosure that can block electromagnetic radiation, such as microwave radiation. A thermally-conductive material 233 is disposed inside the elongated shaft 223 at its distal end 216 directly behind and in contact with the tip 221. In some embodiments, the tip 221 may include a hollow center in which thermally-conductive material 233d is disposed. For example, the thermally-conductive material 233d may be a high thermally-conductive gel.

The thermally-conductive material 233 may have high thermal conductivity, but low electrical conductivity. The thermally-conductive material 233 may include gold, silver, copper, a thermally-conductive gel or polymer, or any combination of these materials. A temperature sensor 231, such as a thermistor or thermocouple, is disposed inside the thermally-conductive material 233 in such a way as to be electrically isolated from the electrically-conductive tip 221 and elongated shaft 223. The temperature sensor 231 may be affixed within the tissue sensor probe 200 using a thermally-conductive adhesive or epoxy. The thermally-conductive material 233 rapidly transfers heat from the body tissue to the temperature sensor 231 to provide accurate and precise temperature measurements of the body tissue.

The temperature sensor 231 is connected to electrically-insulated leads 235, such as wires coated with plastic insulation or a vapor-deposited insulator. The wires 235 emerge from the thermally-conductive material and are coupled to a shielded cable 215 at the proximal end 213 of the tissue sensor probe 200. The wires 235 may twist about each other to form a twisted pair. The far proximal end of the elongated shaft 223 is capped or closed with an electrically-conductive metallic plate 237. A bulkhead-like port 225, which maintains electrical isolation from the external environment, passes through the plate 237 and enables a transition to the shielded cable 215. The twisted pair of tissue sensor probe wires 235 passes through the port 225 into the shielded cable 215. The shield of the cable 215 may be a wire braid or solid cylindrical conductor. An ergonomic handle 227, such as molded plastic that provides an attractive device appearance, is positioned at the proximal end 213 of the tissue sensor probe 200.

Thus, the cylindrical elongated shaft 223, the tip 221, and the cap 237 form an electrically-conductive enclosure that isolates the temperature sensor 231 from any electromagnetic interference external to the tissue sensor probe 220. At the same time, the thermally-conductive tip 221 and the thermally-conductive material 233 can quickly transmit thermal energy at or near the exterior of the tissue sensor probe 200 to the temperature sensor 231 to ensure a fast thermal response by the temperature sensor 231.

The type of electrically-conductive material used to form the cylindrical elongated shaft 223, the tip 221, and the cap 237, and other parameters of the electrically-conductive material (e.g., thickness) may be selected based on parameters of electromagnetic radiation emitted by the microwave probe (e.g., frequency, phase, or polarization). The parameters for the electrically-conductive material may also be selected based on parameters of the electromagnetic radiation from another source.

The surgical ablation system may include multiple tissue sensor probes 200. The tissue sensor probes 200 may be placed at the margin of a target tissue structure to make sure that critical tissue structures are not harmed by elevated temperatures created by a microwave ablation probe (e.g., ablation probe 200).

Figure 4:
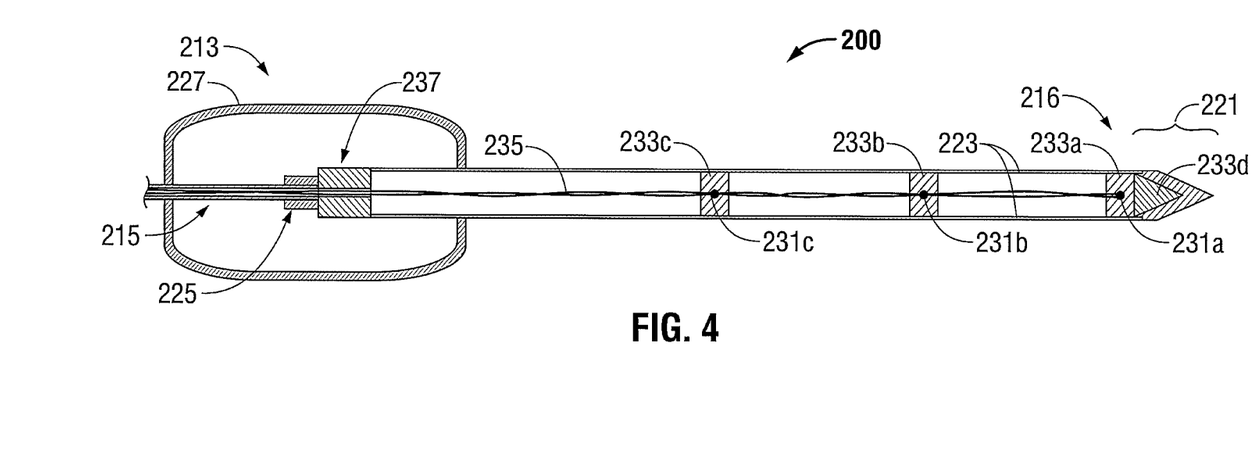
FIG. 4 is a side, cross-sectional view of a tissue sensor probe in accordance with other embodiments of the present disclosure.

FIG. 4 illustrates a side, cross-sectional view of a tissue sensor probe 200 in accordance with another embodiment of the present disclosure. The thermally-conductive material 233d may extend within a hollow portion of the tip 221. Thermally-conductive material 233b, 233c may also be disposed within the elongated shaft 223 at different positions along the length of the elongated shaft 223. Temperature sensors 231b, 231c are disposed within the thermally-conductive material 233b, 233c and connect to the leads or wires 235. In this configuration, the temperature of tissue near each temperature sensor 233a-233c may be measured to obtain a temperature gradient or profile of the tissue along the length of the elongated shaft 223. For example, the tissue sensor probe 200 may be oriented parallel to an ablation probe to measure the temperature radiating up the ablation probe. To ensure accurate temperature measurements, the elongated shaft 223 or those portions of the elongated shaft 223 that make contact with the thermally-conductive material 233b, 233c may be made of a thermally-conductive material.

The probe 200 may include one or more absorbent sleeves 214 disposed on the elongated shaft 223 and adapted to attract and absorb moisture, e.g., steam and/or condensed water vapor, which may be released as a byproduct of an ablation procedure and collect on the elongated shaft 223. In some embodiments, absorbent sleeve(s) 214 is slidably disposed on the elongated shaft 223 to enable the selective absorption of moisture, and/or to enable a surgeon to position sleeve 214 according to surgical requirements. Sleeve(s) 214 may be formed from any suitable biocompatible absorbent material, including without limitation paper-based material composed of virgin wood pulp that is obtained from certified forests.

Probe 200 includes a handle 227 positioned at a proximal end 213 of the probe 200. Handle 227 may include grip-enhancing features such as, without limitation, knurling, ridges, coatings (e.g., silicone-based or rubberized coating) disposed on at least a part of an outer surface of the handle 227. Probe 200 includes a cable 215 extending from the probe 200 that is adapted to operatively couple the temperature sensor 231 with temperature sensor circuit 35. The elongated shaft 223 of the probe 200 may have any suitable length and/or diameter suitable for use in an ablation procedure. In some embodiments, the elongated shaft 223 has a length of about 10 cm to about 30 cm.

Tissue sensor probe 200 includes a temperature sensor 231 disposed at a distal end 211 of the probe shaft 223. Temperature sensor 231 may include any suitable temperature-sensing transducer, including without limitation, a fluoroptic (e.g., fiber optic) sensor, a thermocouple, a thermistor, an infrared thermometer (e.g., emissive measurement), a resistance thermometer (also referred to as a resistive temperature detector or resistive thermal device (RTD)), or other temperature sensor now or in the future known. Temperature sensor 231 is operatively coupled to temperature sensor circuit 35 via connection element 218, which may include electrical and/or fiber optic conductors. Temperature sensor circuit 35 is adapted to receive a temperature measurement signal from temperature sensor 231 to determine a tissue temperature, which, in turn, may be utilized by controller 30 and/or generator 20.

Figure 5:
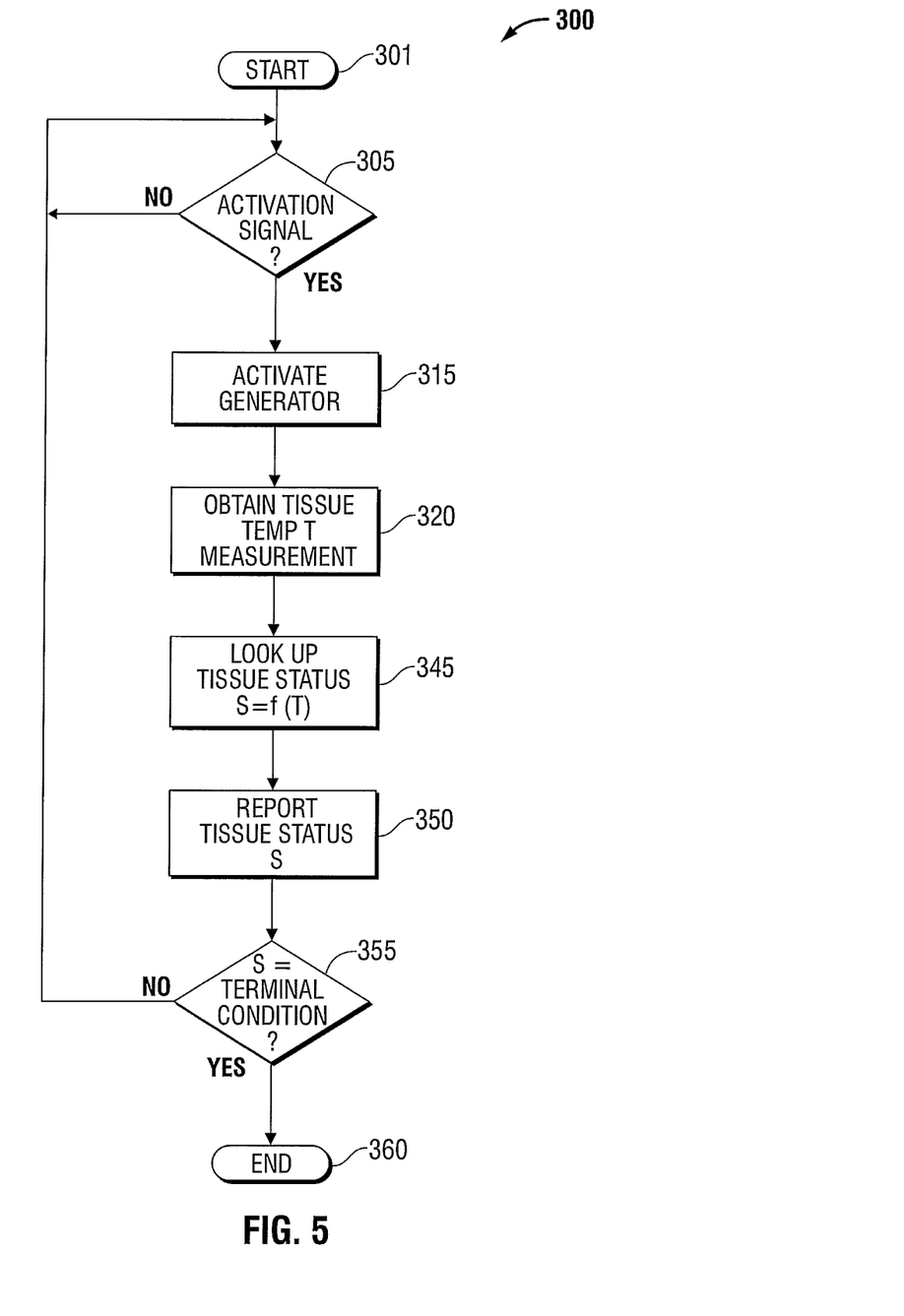
FIG. 5 is a flowchart showing a method of operation of a microwave ablation system having a tissue sensing probe in accordance with embodiments of the present disclosure.

FIG. 5 illustrates a method 300 for operating a microwave ablation system 10, which includes the generator 20, the controller 30, the ablation probe 100, and the tissue sensor probe 200. The method 300 begins in step 301 wherein one or more initializations may be performed, e.g., power-on self test (POST), memory allocation, input/output (I/O) initialization, and the like. In step 305, it is determined whether an activation signal is present, e.g., whether actuator 40 has been engaged by a user to cause delivery of ablation energy to the tissue. If no activation signal is present, the process iterates until an activation signal is detected (e.g., the system enters a "wait state").

Upon receipt of an activation signal, an ablation generator, e.g., generator 20, is activated in step 315 to deliver ablation energy to tissue via the ablation probe 100. In step 315, an ablation control signal may be generated by controller 30 and conveyed to ablation generator 20 via generator interface 37. In step 320, a tissue temperature measurement T is obtained. Tissue temperature measurement T is obtained from temperature sensor 231 of tissue sensor probe 200.

In step 345, a tissue temperature measurement is used to determine a tissue status S. Tissue status S may be indicative of whether the sensed tissue has received insufficient, sufficient, and/or excessive ablation energy, e.g., whether the tissue is underablated ("undercooked"), ablated ("cooked"), or hyper-ablated ("charred"). Other tissue statuses are envisioned, for example, a near-ablated ("pre-cooked") status. A lookup table (not explicitly shown) may be utilized to ascertain tissue status based upon temperature. In other embodiments, the lookup table may be used to ascertain tissue status based upon temperature, permittivity, and loss factor. For example, the lookup table may have a three-dimensional organization whereby a first table dimension is representative of tissue temperature, a second table dimension is representative of tissue permittivity, and a third table dimension is representative of tissue loss factor. In this manner, each of temperature, permittivity, and loss factor are thus used as indices into the three dimensional table to identify a particular tissue status corresponding thereto. In some embodiments, the lookup table may be included within database 33.

In step 350, a tissue status signal may be reported to a user via any suitable manner of communication, such as without limitation, an audible signal, a visual signal, a haptic (tactile) signal, and/or a combination of these signals. By way of example only, an underablated status may be excluded from reporting, since this is routinely observed and expected during an initial phase of an ablation procedure. As tissue approaches ablated status, e.g., attains near-ablated status, a first tissue status signal, e.g., a short audible signal, may be issued to apprise a user accordingly. When tissue reaches ablated status, a second tissue status signal may be issued, e.g., a more urgent audible signal, alone or in combination with a visual signal. In some embodiments, multiple tissue statuses may be utilized to convey a continuous indication of ablation progress. In this manner, a user may be assisted in the accurate and timely assessment of ablation progress, in real-time, during an ablation procedure.

A tissue status may be associated with a terminal condition whereby attainment of a terminal status indicates that the ablation procedure is complete and/or that delivery of ablation is to be terminated. In step 355, a determination is made whether the currently-identified tissue status is a terminal status. If the current tissue status is not a terminal status, the process iterates step 305 whereupon presence of an activation signal is confirmed, and the ablation procedure continues as just described. Conversely, if a terminal status is reached, the ablation process concludes at step 360.

It is to be understood that the steps of the method provided herein may be performed in combination and/or in a different order than presented herein without departing from the scope and spirit of the present disclosure.

During use, tissue sensor probe 200 is positioned at a boundary of the operative site that corresponds to an outer limit of the desired ablation region. As ablation energy is applied to targeted tissue (e.g., generator 20 is activated and ablation probe 100 is applied to the operative site), tissue sensor probe 200 provides tissue parameters (e.g., temperature and dielectric properties) to controller 30. As the ablated region expands, controller 30 continues to monitor tissue status at the probed location. When a tissue terminal status is detected (e.g., tissue is "cooked"), controller 30 causes generator 20 to be deactivated, thus enabling a surgeon to perform a precisely-formed ablation, which may lead to improved operative outcomes, reduced operative and/or recovery times, and enhanced patient satisfaction. A distal end 216 of tissue sensor probe 200 may be generally positioned coincident with a plane radially extending transversely from feed point 122 of the ablation probe 100.

Tissue sensor probe 200 may be positioned between an ablation region and an adjacent anatomical structure, which may be a critical structure to be protected from receipt of excessive ablation energy, increased temperature, and/or undesired denaturization which may occur as a side effect of an ablation procedure. In this instance, a tissue terminal status may reflect a threshold at which an ablation procedure is suspended in order to protect a critical structure from damage.

The described embodiments of the present disclosure are intended to be illustrative rather than restrictive, and are not intended to represent every embodiment of the present disclosure. Further variations of the above-disclosed embodiments and other features and functions, or alternatives thereof, may be made or desirably combined into many other different systems or applications without departing from the spirit or scope of the disclosure as set forth in the following claims both literally and in equivalents recognized in law. The claims can encompass embodiments in hardware, software, or a combination thereof.

What is claimed is:

1. An electromagnetic surgical ablation system, comprising:
    a generator that selectively provides surgical ablation energy to an ablation probe;
    an ablation probe operatively coupled to the generator and configured to receive ablation energy from the generator and to deliver the ablation energy to tissue;
    a controller operatively coupled to the generator, including:
        a processor; and
        a memory operatively coupled to the processor; and
    a tissue sensor probe operatively coupled to the controller, including:
        an electrically-conductive enclosure, at least a portion of the electrically-conductive enclosure formed of a thermally-conductive material;
        a material of high thermal conductivity disposed in the electrically-conductive enclosure and in thermal association with the thermally-conductive material; and
        a temperature sensor disposed in the material of high thermal conductivity and electrically isolated from the electrically-conductive enclosure.

2. The surgical ablation system of claim 1, wherein the electrically-conductive enclosure includes:
    an elongated cylindrical shaft having a distal end and a proximal end;
    a thermally-conductive tip electrically coupled to the distal end of the elongated cylindrical shaft; and
    a cap electrically coupled to the proximal end of the elongated cylindrical shaft.

3. The surgical ablation system of claim 2, wherein the temperature sensor includes a plurality of temperature sensors disposed along the length of the elongated cylindrical shaft.

4. The surgical ablation system of claim 2, wherein at least a portion of the material of high thermal conductivity is disposed in the thermally-conductive tip.

5. The surgical ablation system of claim 2, wherein at least one of the elongated cylindrical shaft, the thermally-conductive tip, and the cap includes at least one of stainless steel, copper, and aluminum.

6. The surgical ablation system of claim 1, wherein the temperature sensor is configured to provide a temperature sensor signal corresponding to a temperature of body tissue.

7. The surgical ablation system of claim 1, wherein the temperature sensor includes at least one of a fluoroptic temperature sensor, a thermocouple, a thermistor, a resistance temperature detector, or an infrared thermometer.

8. The surgical ablation system of claim 1, wherein the tissue sensor probe includes a handle disposed at a proximal end of the tissue sensor probe.

9. The surgical ablation system of claim 8, wherein the handle includes a grip-enhancing feature.

10. The surgical ablation system of claim 1, further comprising an actuator operatively coupled to the controller and configured to selectively activate the generator.

11. The surgical ablation system of claim 10, wherein the actuator is selected from a group consisting of a handswitch, a footswitch, and an orally-activated switch.

12. The surgical ablation system of claim 1, wherein the material of high thermal conductivity has low electrical conductivity.

13. The surgical ablation system of claim 1, wherein the material of high thermal conductivity includes at least one of silver, gold, carbon nanotube, diamond, copper, aluminum, thermally-conductive gel, and thermally-conductive polymer.

14. A tissue sensor probe, comprising:
- an electrically-conductive elongated cylindrical shaft having a distal end and a proximal end;
- an electrically-conductive tip coupled to the distal end of the electrically-conductive cylindrical shaft to close the distal end of the electrically-conductive cylindrical shaft, the electrically-conductive tip having high thermal conductivity;
- a material of high thermal conductivity disposed in the distal end of the elongated cylindrical shaft, the material of high thermal conductivity in thermal communication with the electrically-conductive tip;
- a temperature sensor disposed in the material of high thermal conductivity and electrically isolated from the electrically-conductive cylindrical shaft and the electrically-conductive tip; and
- an electrically-conductive cap coupled to the proximal end of the elongated cylindrical shaft to close the proximal end of the electrically-conductive cylindrical shaft.

15. The tissue sensor probe of claim 14, wherein the temperature sensor is configured to provide a temperature sensor signal corresponding to a temperature of body tissue.

16. The tissue sensor probe of claim 14, wherein the temperature sensor includes at least one of a fluoroptic temperature sensor, a thermocouple, a thermistor, a resistive temperature detector, or an infrared thermometer.

17. The tissue sensor probe of claim 14, wherein at least a portion of the material of high thermal conductivity is disposed in the electrically-conductive tip.

18. The tissue sensor probe of claim 14, wherein the tissue sensor probe includes a handle disposed at a proximal end of the elongated cylindrical shaft.

19. The tissue sensor probe of claim 14, wherein the material of high thermal conductivity has low electrical conductivity.

20. The tissue sensor probe of claim 14, wherein the material of high thermal conductivity includes at least one of silver, gold, carbon nanotube, diamond, copper, and aluminum.

21. The tissue sensor probe of claim 14, wherein the temperature sensor includes a plurality of temperature sensors disposed along the length of the electrically-conductive elongated cylindrical shaft.

22. The tissue sensor probe of claim 14, wherein at least one of the electrically-conductive elongated cylindrical shaft, the electrically-conductive tip, and the electrically-conductive cap includes at least one of stainless steel, copper, and aluminum.

* * * * *